United States Patent [19]

Penney et al.

[11] Patent Number: 4,784,491

[45] Date of Patent: Nov. 15, 1988

[54] SYSTEM TO PROTECT OPTICS AGAINST DIRTY ENVIRONMENTS

[75] Inventors: Carl M. Penney, Schenectady, N.Y.; Richard M. Lund, Inverness, Fla.

[73] Assignee: General Electric Company, Schenectady, N.Y.

[21] Appl. No.: 870,269

[22] Filed: Jun. 3, 1986

[51] Int. Cl.4 .............................................. G01B 11/24
[52] U.S. Cl. .................... 356/376; 350/584; 219/124.34; 219/121.84
[58] Field of Search ............... 356/376; 350/582, 584; 219/121 FS, 121 LC, 124.34

[56] References Cited

U.S. PATENT DOCUMENTS 1,869,350 7/1932 Lincoln ............................. 219/123
3,373,752 8/1968 Inoue .............................. 219/121 FS
3,519,334 7/1970 Heitmann et al. ............... 219/121 FS
3,749,878 7/1973 Sullivan et al. .................. 219/121 FS
4,488,032 12/1984 Case, Jr. et al. ................. 219/124.34

Primary Examiner—R. A. Rosenberger
Assistant Examiner—Crystal Copper
Attorney, Agent, or Firm—Donald R. Campbell; James C. Davis, Jr.; Paul R. Webb, II

[57] ABSTRACT

An optical sensor head has deep, pitched grooves or screw threads in the walls of the gas channel, and a gas flow swirled along the grooves to protect optics against atmospheric debris and moving particles such as is generated by an industrial process. The grooves are pitched to support swirling motion of the gas. Use of swirled flow increases allowable flow velocity and diverts incoming particles toward the channel walls. The windows of an optical profiler, for instance, are protected against the smoke and weld spatter created by a metal-inert-gas welding torch.

8 Claims, 3 Drawing Sheets

SYSTEM TO PROTECT OPTICS AGAINST DIRTY ENVIRONMENTS

BACKGROUND OF THE INVENTION

This invention relates to protecting optical components against an atmosphere containing moving particles and other debris, and more particularly to an optical sensor and profiler which is shielded from the smoke and weld spatter generated by an arc welding process.

The use of optical sensors to guide industrial processes is increasing rapidly. One of the major problems encountered in this trend is maintaining the transmission of those optical elements which form the window through which the sensor views the industrial process. This problem can be substantial even with clean processes because of dust and smoke normally found in the work place. However, when a sensor must observe directly a process producing smoke, spatter or other airborne debris, the problem of window cleanliness can become critical, requiring that the process be stopped frequently to clean or change windows, or that some type of refreshable window mechanism or shutter be installed. Optical sensors used for weld groove tracking and weld quality control are good examples of devices which should tolerate a dirty atmosphere. A reasonable goal is that windows should remain clean at least until some procedure required by the process, such as placing another spool of wire on a MIG (metal inert gas) weld system, or a natural work division such as a change of shift provides a maintenance opportunity Furthermore, maintenance should be inexpensive and easy to implement. The present window and optics protection system meets these goals.

Window protection is used in various optical applications, of which laser machining and medical cutting operations form good general examples. A common protection mode is to flow gas around the optical element facing the exterior of the device, and thence down an elongated channel (see FIG. 1). The drag of the out-flowing gas serves to stop most smoke, particles and other debris from flowing up through the opening and contacting the optical element. However, in the case of most MIG welding operations and other industrial operations such as grinding, particles are driven with substantial speed toward the optics, while light economy requires openings at least several millimeters in diameter. In such cases it was found that sufficient gas flow to stop most of the particles from reaching the optics is either difficult to support or disturbs the process. Thus the approaches used in the prior art to protect optics are either insufficient, inconvenient, or disrupt the process when applied, for instance, to MIG welding.

SUMMARY OF THE INVENTION

It has been found that a practical gas flow swirled down a much shorter gas channel than just described, and a channel that has deep grooves in the walls pitched to support the swirling motion of the gas, is more effective to divert incoming particles and debris and prevents deposition on the window or other external optical component.

According to one aspect of the invention, an optical sensor head with improved protection against atmospheric debris is comprised of a housing containing optical components and having an inlet to supply gas which flows past the exterior optical component to the gas channel. Means are provided inside the housing to impart swirling motion to the gas, and the gas channel has in its walls relatively deep grooves, preferably screw threads, pitched in the direction of gas motion as it swirls toward the opening. Moving particles, smoke and debris such as is generated by an industrial process are turned toward the grooved wall and prevented from depositing on the optics, maintaining good light transmission. The means to impart swirling motion to the gas is illustratively a gas nozzle next to the window having tangential channels for passage of gas at high velocity from the periphery to the central bore.

The preferred embodiment is an optical profiler head for weld groove tracking which is comprised of an optical transmitter to project a structured light pattern onto the workpiece and an optical receiver that relays an image of the region in front of the weld puddle to a remote television-like camera. The windows in both parts are protected from the smoke and weld spatter produced by a MIG welding torch by the system just described.

DETAILED DESCRIPTION OF THE INVENTION

Figure 1:
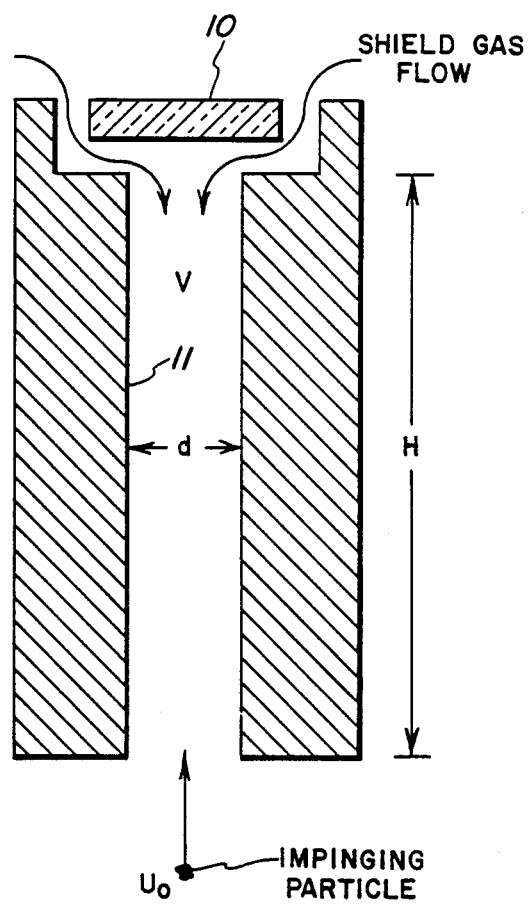
FIG. 1 shows a prior art configuration for protecting a window from atmospheric debris.

Obervations of steel weld spatter have indicated that in a typical MIG welding operation, the predominant number of spatter particles lie within 0.1 and 0.3 mm in diameter, and move away from the weld puddle with initial velocities within the range of 1 to 10 meters per second. It has been found that these particles stick when they strike a glass plate, but bounce nearly elastically off many metal surfaces. A long channel of gas flowing at practical velocities is required to stop such particles as can be seen in FIG. 1. which shows a standard configuration for protecting a window from atmospheric debris. Here shield gas flows past a window 10 into a channel 11 of width d and height H. The shield gas velocity is directed down the channel with a magnitude V. A particle impinges on the channel with upward velocity U, initially equal to $U_o$. The channel height needed to stop the particle before it hits the window is determined from the equation $Z = U_o^2 \tau / 2V$, where $\tau$ is the drag coefficient. This equation is interpreted for Z set equal to H, indicating a particle just stopped.

A typical spatter particle from steel welding will have a diameter of 0.3 mm and will leave the region of the weld puddle with an initial velocity of 200 cm/sec. The maximum shield gas flow can be limited by cost of the gas, convenience of introducing it, or interference with the weld process. The latter limitation is often the most stringent, and welding interference has been found at flows greater than 50 standard cubic feet per hour (about 400 ml/sec). Using these values it follows that H is approximately equal to $10\ d^2$. Thus a window with a 1 centimeter diameter would require a 10 centimeter long channel for protection against weld spatter at maximum allowable shield gas flow rates near the weld.

In accordance with this invention a practical gas flow swirled down a much shorter, deeply threaded or deeply grooved channel will stop this kind of particle flux. It was demonstrated that a window was protected by this configuration during an arc-on exposure time of one hour. In this case, the window channel was 1" in diameter, and 2" long, with a gas flow of only 10 standard cubic feet per hour. An optical profiler has been designed with a gas channel ¾" in diameter and 1½" long. Typically the length of the gas channel is no greater than twice its diameter. The effectiveness of this configuration arises from the combination of several principles which are explained later.

Figure 2:
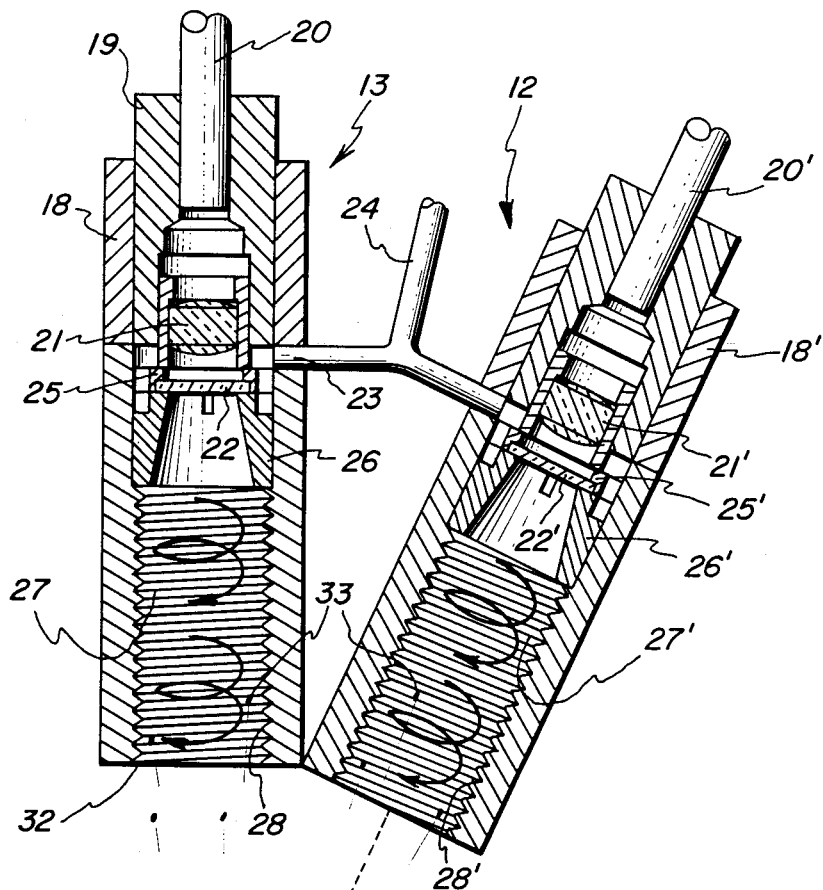
FIG. 2 is a schematic vertical cross section of a triangulation optical profiler having improved protection against smoke and weld spatter during a welding operation.

FIG. 2 shows an illustrative embodiment of the invention, a triangulation optical profiler used for MIG weld groove tracking. The profiler head is comprised of an optical transmitter and an optical receiver indicated generally at 12 and 13. The first projects a structured light pattern such as light stripe 14 onto the workpiece 15 intersecting the groove or joint 16 a short distance ahead of the weld puddle 17. The receiving optical unit images the light stripe and groove and surrounding region of the workpiece. Structured light is relayed to the optical profiler head from a remote laser source, and the groove location image is transmitted back to a remotely located television-like camera, over separate coherent fiber optic bundles. Optical receiver 13 is described in detail and corresponding parts in optical transmitter 12 are identified by corresponding primed numerals.

A metal housing 18 has at its upper end a support column 19 which holds coherent fiber optic bundle 20. An optical lens system 21 and a transparent window 22, the exterior optical component, are suitably mounted in alignment inside the housing such that the lens system views the weld seam through the window and focuses the image on the entrance of fiber optic bundle 20. The housing has a gas inlet 23 to admit shield gas, or nitrogen or filtered air, to the inside of the housing in the space between the lens and window. As illustrated here, shield gas is supplied to the optical profiler head through inlet tube 24.

Shield gas flows past window 22 and through holes in the periphery of a window mount 25 into a gas nozzle 26 which imparts swirling motion to the shield gas. A gas channel 27 at the lower end of housing 18 has in its walls internal relatively deep grooves or threads 28 pitched in the direction of gas motion as it swirls toward the exit of the channel. The threads are pitched to support the rotation of the gas.

Figure 3:
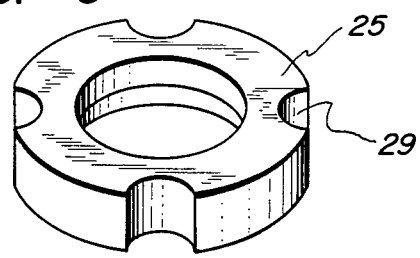
FIG. 3 is an isometric view of the window mount.
Figure 4:
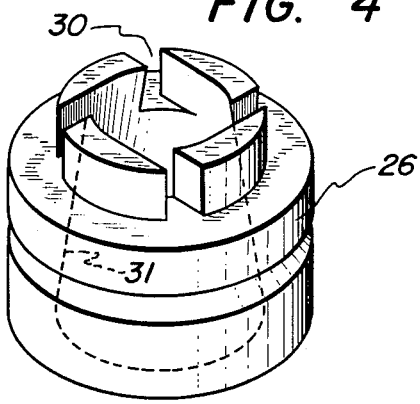
FIG. 4 is an isometric view of the profiler part which imparts a swirling motion to the shield gas.

Window mount 25, see FIG. 3, has four equally spaced peripheral openings 29 to allow passage of shield gas to gas nozzle 26, shown in greater detail in FIG. 4. The reduced diameter upper part of the gas nozzle has four equally spaced, 45° tangential slots 30 exiting into a central tapered bore 31. The gas nozzle is held against the lower surface of window 22 which encloses the tangential gas channels 30. A spiral motion is imparted to the gas as it flows at high velocity through these tangential channels 30, swirling down the central bore 31 into the deeply threaded gas channel 27. Window mount 25 and gas nozzle 26 are made, for instance, of anodized aluminum.

The several principles which in combination render this a more effective configuration to protect the optics against smoke and weld spatter are now explained. Because of the swirl motion imparted to the gas by gas nozzle 26, the gas can be given much higher velocity for the same flow rate, increasing its ability to divert moving particles. The particles, under the action of centrifugal force caused by the rotation of the gas, are turned toward the walls of gas channel 27 by the swirling gas, where they strike deeply grooved threads 28 which are pitched in the direction of gas motion as its swirls toward the opening 32. The pitch of the threads supports rotation of the gas, while the angled sides of the grooves encourage particles 33 to bounce back out of the channel. Some of the particles are deposited on the threaded channel wall. This configuration is highly effective in preventing deposition of the atmospheric debris on the external optical component. The novel features are the use of deep grooves to encourage particles to bounce away and be diverted from the window, the use of swirled gas flow to increase allowable flow velocity and divert particles toward the channel walls, and use of grooves pitched to support swirling motion of the gas. With this configuration the gas has a high velocity; it does not take a large gas supply. The rotating shield gas discharged by the optical profiler is not a directed flow, that can disrupt a weld puddle or other similar process close to the region observed. An incidental advantage of this configuration is that the threads 28 trap light and reflected light does not get into the receiving objects.

This invention has been described with respect to MIG welding applications and was reduced to practice on an optical profiler used for MIG weld groove tracking. However, there are many other applications for optical sensors which benefit from the excellent optical protection provided by this system.

While a specific embodiment of the invention has been illustrated and explained, it will be understood by those skilled in the art that various changes in form and details may be made. The appended claims are intended to cover all such modifications and changes that fall within the true spirit and scope of the invention.

The invention claimed is:

1. An optical sensor head having improved protection against atmospheric debris comprising:
   a housing containing optical components and having an inlet to admit gas which flows past an exterior optical component to a gas channel;
   means in said housing to impart spiral swirling motion to said gas;
   said gas channel having internal relatively deep grooves pitched in the direction of gas motion as it rotates and swirls toward an exit opening;
   whereby incoming particles, smoke and other atmospheric debris generated by an industrial process are turned toward the grooved wall of said gas channel and prevented form depositing on said exterior optical component.

2. The sensor head of claim 1 wherein the length of said gas channel is no greater than twice its diameter.

3. The sensor head of claim 1 wherein said means to impart swirling motion is a gas nozzle having tangential slots for passage of gas at high velocity.

4. The sensor head of claim 3 wherein said exterior optical component is a transparent window held in a window mount which has peripheral openings to pass gas into said tangential slots.

5. The sensor head of claim 1 wherein said means to impart swirling motion is a gas nozzle having tangential slots for passage of gas into a central bore which opens into said gas channel, and wherein said deep gas channel grooves are threads.

6. An optical profiler head having improved protection against weld spatter and smoke comprising:
   an optical transmitter to project a structured light pattern onto a weld groove and an optical receiver to image the foregoing, said transmitter and receiver each comprised of:
   a coherent fiber optic cable, an optical lens system and a transparent window mounted in alignment in a housing that has an inlet for gas which flows past said window to a cylindrical gas channel;
   means in said housing to impart swirling motion to said gas;
   said gas channel having in the walls thereof deeply grooved threads pitched in the direction of gas motion as it rotates and swirls toward the exit opening of said channel;
   whereby incoming weld spatter and smoke and other debris generated by a welding process are turned toward the threaded channel wall and prevented from dirtying said window.

7. The profiler head of claim 6 wherein said means to impart swirling motion is a gas nozzle having tangential channels for passage of gas to a central bore which opens into said gas channel.

8. The profiler of claim 6 wherein said window is in a window mount which has peripheral openings, and said means to impart swirling motion is a gas nozzle having tangential slots enclosed by said window such that gas passes through said peripheral openings and through said tangential slots to a central bore which opens into said gas channel.

* * * * *